United States Patent
Lobbestael et al.

(10) Patent No.: US 10,806,386 B2
(45) Date of Patent: Oct. 20, 2020

(54) TISSUE SITE DETECTION

(71) Applicant: Nonin Medical, Inc., Plymouth, MN (US)

(72) Inventors: Aaron Alfred Lobbestael, Watertown, MN (US); Gregory J. Rausch, Minnetonka, MN (US); Nicholas J. Kanavati, Minneapolis, MN (US)

(73) Assignee: Nonin Medical, Inc., Plymouth, MN (US)

(*) Notice: Subject to any disclaimer, the term of this patent is extended or adjusted under 35 U.S.C. 154(b) by 266 days.

(21) Appl. No.: 15/515,530

(22) PCT Filed: Sep. 29, 2015

(86) PCT No.: PCT/US2015/052800
§ 371 (c)(1),
(2) Date: Mar. 29, 2017

(87) PCT Pub. No.: WO2016/053942
PCT Pub. Date: Apr. 7, 2016

(65) Prior Publication Data
US 2017/0224263 A1    Aug. 10, 2017

Related U.S. Application Data

(60) Provisional application No. 62/057,057, filed on Sep. 29, 2014.

(51) Int. Cl.
*A61B 5/1455* (2006.01)
*A61B 5/1495* (2006.01)
*A61B 5/00* (2006.01)

(52) U.S. Cl.
CPC ........ *A61B 5/14552* (2013.01); *A61B 5/1495* (2013.01); *A61B 5/14551* (2013.01);
(Continued)

(58) Field of Classification Search
CPC .......... A61B 2560/0223; A61B 5/1495; A61B 5/6802; A61B 5/684; A61B 2562/0238; A61B 5/0059
See application file for complete search history.

(56) References Cited

U.S. PATENT DOCUMENTS

| 5,058,588 A | 10/1991 | Kaestle |
| 2004/0122301 A1 | 6/2004 | Kiani et al. |

(Continued)

FOREIGN PATENT DOCUMENTS

WO    WO-2016053942 A1    4/2016

OTHER PUBLICATIONS

"International Application Serial No. PCT US2015 052800, International Preliminary Report on Patentability dated Apr. 13, 2017", 6 pgs.

(Continued)

*Primary Examiner* — Christine H Matthews
(74) *Attorney, Agent, or Firm* — Schwegman Lundberg & Woessner, P.A.

(57) ABSTRACT

A device includes a housing, an emitter, a detector, and a processor. The housing has a body contact surface. The emitter is coupled to the housing and has an emission surface and has an electrical terminal. The emission surface is configured to emit light proximate the body contact surface in response to a signal applied to the electrical terminal. The detector is coupled to the housing. The detector has a sense surface and an output terminal. The detector is configured to provide an output signal on the output terminal in response to light detected at the sensor surface. The processor is configured to implement an algorithm to determine a tissue site based on the emitted light and based on the detected light.

6 Claims, 2 Drawing Sheets

(52) U.S. Cl.
CPC ............ *A61B 5/681* (2013.01); *A61B 5/684* (2013.01); *A61B 5/6802* (2013.01); *A61B 2560/0223* (2013.01)

(56) References Cited

U.S. PATENT DOCUMENTS

| | | |
|---|---|---|
| 2008/0221410 A1 | 9/2008 | Campbell et al. |
| 2011/0288384 A1 | 11/2011 | Ali et al. |
| 2012/0083705 A1 | 4/2012 | Yuen et al. |
| 2012/0190946 A1 | 7/2012 | Bernreuter |
| 2012/0259190 A1 | 10/2012 | Baker, Jr. |

OTHER PUBLICATIONS

International Application Serial No. PCT/US2015/052800, International Search Report dated Dec. 28, 2015, 2 pgs.
International Application Serial No. PCT/US2015/052800, Written Opinion dated Dec. 28, 2015, 8 pgs.

US 10,806,386 B2

TISSUE SITE DETECTION

CLAIM OF PRIORITY

This patent application is a U.S. National Stage Filing under 35 U.S.C. 371 from International Application No. PCT/US2015/052800, filed on Sep. 29, 2015, and published as WO 2016/053942 A1 on Apr. 7, 2016, which claims the benefit of priority of U.S. Provisional Patent Application Ser. No. 62/057,057, filed on Sep. 29, 2014, each of which is hereby incorporated by reference herein in its entirety.

BACKGROUND

A variety of physiological parameters can be used to provide a measure of health for a patient. One such measurement is oxygen saturation (commonly referred to as $SpO_2$) which relates to a measure of oxygenation of blood. Another example includes regional oxygen saturation (commonly referred to as $rSO_2$) which relates to oxygenation of a region or tissue. Oxygenation can be determined using a system of optical emitters and optical detectors along with suitable processing.

Accurate measurement of oxygenation can be very important for health or safety. Accuracy of the oxygenation measurement is influenced by device calibration factors. Approaches to determining or selecting calibration factors have been inadequate.

OVERVIEW

The present inventors have recognized, among other things, that a problem to be solved can include determining calibration coefficients for accurate oxygenation measurement. The calibration coefficients are influenced by tissue characteristics or by the tissue site. The present subject matter can help provide a solution to this problem, such as by determining the site of the tissue.

Tissue characteristcs or tissue site information can be helpful for purposes in addition to selecting calibration coefficients for oxygenation measurement. For example, tissue site information can be useful for determining appropriate signal filters or for measuring motion of a particular site.

A device includes a housing, an emitter, a detector, and a processor. The housing has a body contact surface. The emitter is coupled to the housing and has an emission surface and has an electrical terminal. The emission surface is configured to emit light proximate the body contact surface in response to a signal applied to the electrical terminal. The detector is coupled to the housing. The detector has a sense surface and an output terminal. The detector is configured to provide an output signal on the output terminal in response to light detected at the sensor surface. The processor is configured to implement an algorithm to determine a tissue characteristic or site based on the emitted light and based on the detected light.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
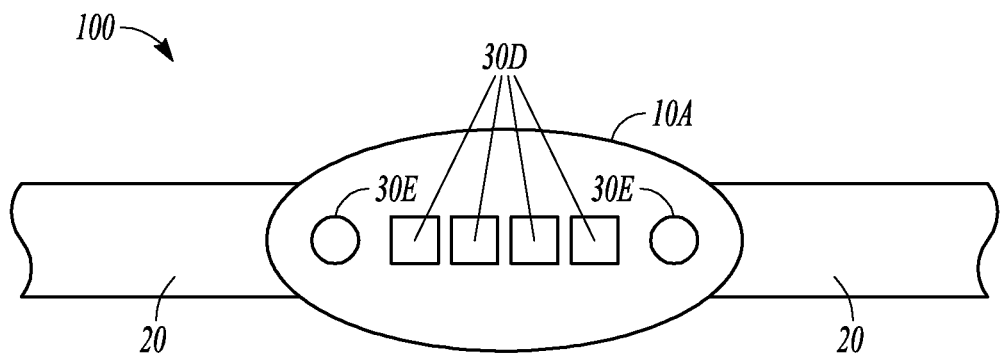
FIG. 1 includes a view of a sensor, according to one example.

FIG. 1 includes a view of system 100 having sensor 10A, according to one example. Sensor 10A includes a housing and is coupled to belt 20. Belt 20 can be configured to encircle a portion of a body site and position sensor 10A at a particular tissue site. Sensor 10A includes a contact surface, and in the example shown, includes two emitters, here denoted as emitters 30E, and includes four detectors, here denoted as detectors 30D. Other arrangements and numbers of optical elements (emitters and detectors) are also contemplated.

Belt 20 can include other elements not shown in this figure, including an elastic element, an adjustor, a buckle or other fastener. Belt 20 can be fabricated of a textile product or other materials such as leather, fabric, or a polymer. Belt 20 can include a wrap or a bandage.

Figure 2:
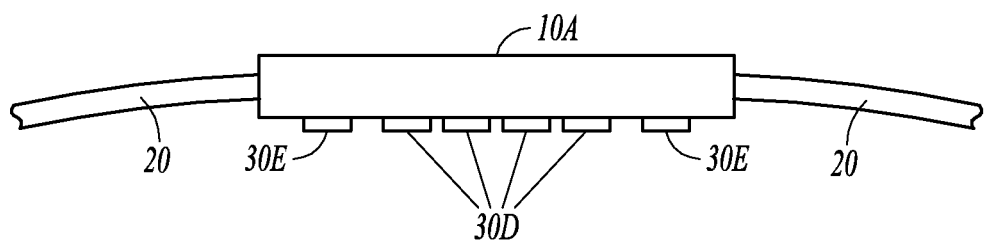
FIG. 2 includes a view of a sensor, according to one example.

FIG. 2 includes a side view of sensor 10A and belt 20, according to one example. In the figure, emitters 30E can each include a single light emitting diode (LED) or include more than one LED. In addition, any particular LED can emit light having a single wavelength, multiple discrete wavelengths, or a spectrum of wavelengths. Emitters 30E and detectors 30D are located on a contact surface.

Figure 3:
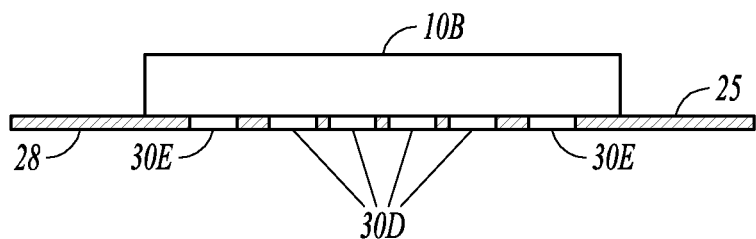
FIG. 3 includes a view of a sensor, according to one example.

FIG. 3 includes a view of sensor 10B, according to one example. Sensor 10B includes membrane 25 and includes emitters 30E and detectors 30D. Membrane 25 includes a planar material and has a contact surface 28. Contact surface 28, in one example, is configured as an adhesive surface for bonding to a tissue site. Membrane 25 can be rigid or flexible and can include a polymer material, a textile product, or other material. In one example, emitters 30E and detectors 30D are positioned within membrane 25. In other examples, emitters 30E and detectors 30D are positioned below sensor 10B and within an aperture of membrane 25, and as such, can be described as having a position not within membrane 25.

Figure 4:
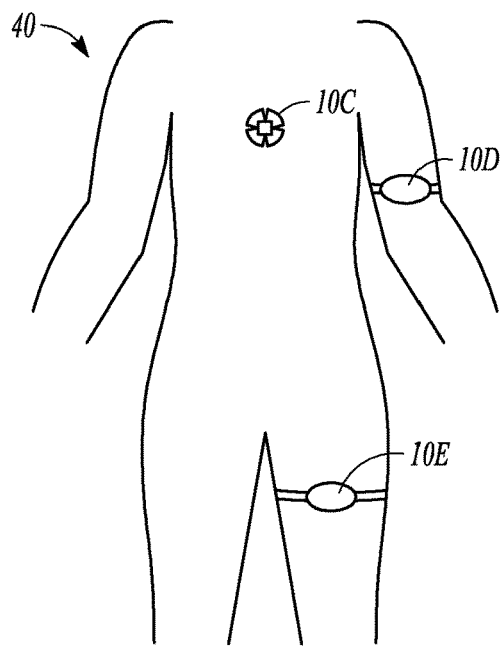
FIG. 4 includes a view of a user fitted with a plurality of sensors, according to one example.

FIG. 4 includes a view of user 40 fitted with a plurality of sensors, according to one example. Sensor 10C is affixed at a tissue site at the chest of user 40 and in the example shown, is in the form of a patch and is coupled to the site by an adhesive. Sensor 10D is affixed at a tissue site on a bicep of user 40 and sensor 10E is affixed at a thigh of user 40. Sensors 10C, 10D, and 10E are attached using a belt or strap, however, in other examples, attachment mechanisms include adhesive, a clamp, and a garment (such as a sock, footwear, shirt, hat, scarf, or pants). The figure shows a user fitted with more than one sensor and in a particular instance, a user can be fitted with a single sensor or more than one sensor.

Figure 5:
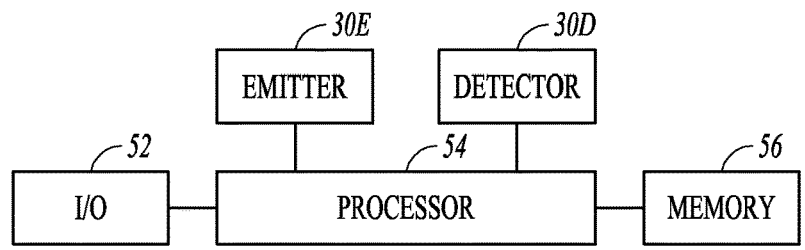
FIG. 5 includes a block diagram of a system, according to one example.

FIG. 5 includes a block diagram of system 50, according to one example. System 50 is configured for affixation to tissue at a site. System 50 is non-invasive and includes input/output module 52, processor 54, memory 56, and optical emitter 30E and optical detector 30D.

Input/output module 52 can include a power switch, a mode control switch, a display, a user-control, a touchscreen, an indicator light, or other interface elements that enable a user to interact with system 50. Input/output module 52 can include a wireless interface to allow communication with a remote device.

Processor 54 can include an analog processor. In one example, processor 54 includes a digital processor and is configured to execute instructions for implementing an algorithm. The instructions and data can be stored in memory 56. Processor 54 can include an analog front end having an amplifier, a filter, a sample and hold circuit, an analog-to-digital converter (ADC), a digital-to-analog converter (DAC), an LED driver, or other modules.

Emitter 30E can include a light emitting diode (LED) configured to emit light of a selected wavelength and power. Emitter 30E can include a number of LED elements having different emitted light wavelengths. Detector 30D can include a photodiode.

Light energy emitted by optical emitter 30E can be directed to reflect or pass through tissue. Light detected by optical detector 30D can be suitably processed to generate selected data in accordance with various examples of the present subject matter.

System 50 can be configured for wearing on a body. In this example, system 50 is powered by a portable power supply, such as a battery. System 50 can be affixed to a garment, a patch, or clamp device that remains in close proximity to the body for an extended duration.

Figure 6:
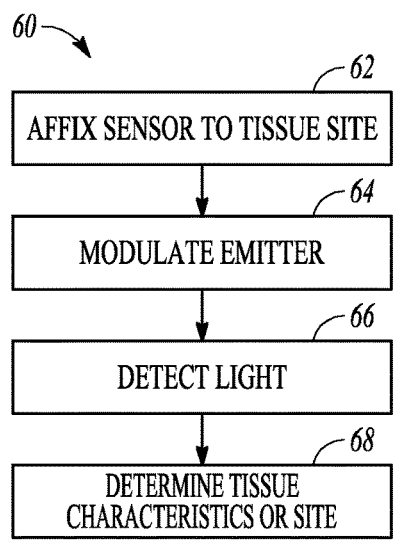
FIG. 6 includes a flow chart of a method, according to one example.

FIG. 6 includes a flow chart of method 60, according to one example. Method 60, at 62, includes affixing a sensor to a tissue site. This can include bonding the sensor to the site using an adhesive. In various examples, this can include donning a garment, such as a shirt, or attaching the sensor using a belt or strap, or bandaging or wrapping a region of the body of the user.

At 64, method 60 includes modulating an emitter, such as emitter 30E, in accordance with an algorithm. The algorithm can be configured to determine a tissue site or configured to measure a physiological parameter. Operation of emitter 30E can be controlled by a processor, such as processor 54.

At 66, method 60 includes detecting light using, for example, detector 30D. A processor, such as processor 54, can be configured to receive an output signal from a detector. The signal from the detector can correspond with the tissue site or can provide data for determining a physiological parameter of the tissue.

At 68, method 60 includes determining a tissue characteristic or site using the emitted light and the detected light. This can include executing an algorithm, some examples of which are described elsewhere in this document. In one example, at 68, method 60 includes determining an algorithm or determining a calibration based on a tissue characteristic or site.

According to one example, the sensor can be affixed using a wrap or a bandage. The sensor can be affixed at, for example, a bicep or a calf. A sensor can also be attached to a tissue site, such as a chest, using a patch or a foam pad. The patch or foam pad can have an adhesive surface.

In one example, a sensor is affixed to a tissue site using an attachment module having encoded information. The attachment module can be configured for affixation to a tissue site and configured to receive a sensor module. In one example, the sensor module can be readily removed and replaced without disturbing or altering the attachment module coupling to the tissue site. In one example, the sensor module can be removed and replaced after having separated the attachment module from the tissue site.

A sensor can be removed for servicing or battery recharging while the attachment module remains affixed to the tissue site. The attachment module is site-specific in that it includes encoded information tailored for a specific site. For example, an attachment module coupled to a belt of approximately 36 inches in length would be suitable for encircling a girth of a user. In a similar manner, an attachment module having relatively small profile contact surface may be tailored for attachment by adhesive to a site such as a chest area of a patient.

The sensor module is configured to read the encoded information associated with the attachment module. In addition, the sensor module is configured to apply calibration coefficients selected from a plurality of calibration coefficients based on the encoded information.

The information in the attachment module can be encoded using a component value (such as a resistance, a capacitance, an inductance, an impedance), using a combination of binary switches or storage registers, micro controller, or other manner of encoding. The sensor module can be configured to receive encoded information from the attachment module by an electrical connection, a reactive coupling (inductive or capacitive), or by an optical coupling.

The sensor may determine the body site and thereby select the appropriate calibration model and coefficients.

In one example, the sensor determines the tissue characteristic or site based on a classification criterion using a vector of quantitative features of an output signal. The output signal can be derived from a photodiode current, a pulse amplitude output or any signal derived from these measures, and, in the following description, is defined as x. Examples of a signal derived from these measures can include a photoplethysmography (sometimes referred to as PPG) waveform detrended with differencing n-times, subtracting a local regression, subtracting a signal mean, a derived value, using a low pass filtering, subtracting an exponential smoother, or normalizing to a scale.

The generalized square distance (Mahalanobis, Euclidean or other similar measure of distance) from each site can be calculated (e.g. $(x-y_t)^T V^{-1} (x-y_t)$, where x is defined above as the vector of features, $y_t$ is a matrix of features for a given site, and V is a covariance matrix or function of the covariance matrix).

The sensor module placement is assigned to the site(s) with the posterior probability defined as $p(s|x)$.

In other examples, machine learning techniques can classify varying influences under which the device is operating allowing customized algorithms and calibration methods. Such learning methods may include perceptron, logistic regression, decision trees, support vector machines, neural networks, principal component analysis, singular value decomposition, eigendecomposition, spectral theorem or Fisher's linear discriminant. Such examples, with the possible addition of kernel methods, can provide topological advantages for classification and computational simplification.

According to one example, a device includes a housing, an emitter, a detector, and a processor. The housing includes a body contact surface configured for affixation to a body at a particular tissue site. The emitter is coupled to the housing and has an emission surface and an electrical terminal. The emission surface is configured to emit light proximate the body contact surface in response to a signal applied to the electrical terminal. A detector is coupled to the housing. The detector has a sense surface and an output terminal. The detector is configured to provide an output signal on the output terminal in response to light detected at the sensor surface. The processor is configured to implement an algorithm to determine a tissue site based on the emitted light and based on the detected light.

The processor can be coupled to a memory and the memory can provide storage for instructions corresponding to the algorithm. In addition, the memory can provide storage for calibration coefficients. The memory can provide storage for a look-up table corresponding to tissue sites and calibration coefficients.

In one example, the algorithm is configured to select a calibration parameter based on the tissue characteristic or site. This can include evaluating an equation to determine coefficients based on a measured parameter associated with the tissue site. The tissue site can be determined, according to one example, based on a vector value. The algorithm can includes determining the tissue site based on an electric current or pulse amplitude at the output terminal. In one example, the algorithm determines a tissue site based on a calculated distance between an electric signal and a stored value.

In one example, the present subject matter is configured to determine an algorithm or determine a calibration based on a detected tissue site. As such, the system determines the location of the sensor and as a function of the location, determines an algorithm or calibration suitable for that site.

A system can include an attachment module and a sensor module. The attachment module can be configured for affixation at a selected tissue site. The attachment module can include a sensor receptor. The attachment module can include encoded information stored thereon. The encoded information is accessible to a communication interface coupled to the sensor receptor. The encoded information is determined by the tissue site.

The sensor module can be configured for placement in the sensor receptor. The sensor module can include a sensor element for determining a physiological parameter corresponding to the tissue site. The sensor element can include an optical detector. The sensor module is configured to couple with the communication interface of the attachment module. The sensor module is configured to access the encoded information and select at least one calibration coefficient corresponding to the encoded information.

The attachment module can include a wrap, an adhesively bonded pad, a belt, a clamp, or a garment. The encoded information can include a component value. The encoded information can include a resistance value, a conductance value, a capacitance value, an inductance value, or an impedance value. In one example, an optical parameter provides the encoded information. An optical parameter can include a modulated power level, a duty cycle, a frequency, a wavelength, or other parameter associated with the optics. The encoded information can include one or more switches or a micro controller.

The communication interface can include an electrical contact, a reactive coupling (such as an inductive coupling or a capacitive coupling) or an optical coupling including an emitter and a detector.

In one example, a system includes different sensors for each tissue site and each tissue site is configured with the calibration information for a particular site.

In one example, a user-operable switch (such as a switch or touch screen) is coupled to the sensor. The user-operable switch is configured to allow the user to select or specify the site location.

Various Notes & Examples

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A device comprising:
   a housing having a body contact surface configured for affixation to a body;
   an emitter coupled to the housing and having an emission surface and having an electrical terminal, the emission surface configured to emit light proximate the body contact surface in response to a signal applied to the electrical terminal;
   a detector coupled to the housing, the detector having a sense surface and an output terminal, the detector configured to provide an output signal on the output terminal in response to light detected at the sensor surface; and
   a processor configured to implement an algorithm to determine a tissue site based on the emitted light and based on the detected light and wherein the algorithm is configured to determine the tissue site based on a vector value.

2. The device of claim 1 wherein the processor is coupled to a memory and wherein the memory includes stored instructions corresponding to the algorithm.

3. The device of claim 1 wherein the algorithm is configured to select a calibration parameter based on the tissue site.

4. The device of claim 1 wherein the algorithm is configured to determine the tissue site based on an electric current or a pulse amplitude at the output terminal.

5. The device of claim 1 wherein the algorithm is configured to determine the tissue site based on a calculated distance between an electric signal and a stored value.

6. The device of claim 1 wherein the algorithm is configured to determine a calibration parameter corresponding to the tissue site.

* * * * *